(12) United States Patent
Tsang et al.

(10) Patent No.: US 8,753,635 B2
(45) Date of Patent: Jun. 17, 2014

(54) MONOCLONAL ANTIBODIES TO ANTHRAX PROTECTIVE ANTIGEN

(76) Inventors: Raymond Tsang, Manitoba (CA); Jody Berry, Manitoba (CA); Xin Yuan, Manitoba (CA); Cindi Corbett, Manitoba (CA); Mike Gubbins, Manitoba (CA); Amin Kabani, Manitoba (CA); Lisa Schmidt, Manitoba (CA)

( * ) Notice: Subject to any disclaimer, the term of this patent is extended or adjusted under 35 U.S.C. 154(b) by 1438 days.

(21) Appl. No.: 12/301,034

(22) PCT Filed: May 17, 2007

(86) PCT No.: PCT/CA2007/000872
§ 371 (c)(1),
(2), (4) Date: May 1, 2009

(87) PCT Pub. No.: WO2007/131363
PCT Pub. Date: Nov. 22, 2007

(65) Prior Publication Data
US 2010/0003263 A1     Jan. 7, 2010

Related U.S. Application Data

(60) Provisional application No. 60/800,831, filed on May 17, 2006.

(51) Int. Cl.
*A61K 39/40* (2006.01)
*A61K 39/395* (2006.01)
*A61K 39/00* (2006.01)
*A61K 39/07* (2006.01)

(52) U.S. Cl.
USPC ............... 424/150.1; 424/130.1; 424/139.1; 424/141.1; 424/178.1; 424/246.1

(58) Field of Classification Search
CPC ............ A61K 2039/507; A61K 2039/00; C07K 14/32; C07K 16/00; C07K 16/1278
See application file for complete search history.

(56) References Cited

PUBLICATIONS

Zhang et al., Biochemical and Biophysical Research Communications, 2006; 341: 1164-1171.*
Ramasamy et al., British Journal of Pharmacology, 2010; 161: 721-748.*
Paul, William E., Fundamental Immunology, 3rd Edition, Raven Press, New York, Chapt. 8, pp. 292-295 (1993), under the heading "Fv Structure and Diversity in Three Dimensions".*
Rudikoff et al. (Proc. Natl. Acad. Sci. USA, 79(6):1979-1983, Mar. 1982).*
Colman P. M. (Research in Immunology, 145:33-36, 1994).*
Bendig M. M. (Methods: A Companion to Methods in Enzymology, 1995; 8:83-93).*
MacCallum et al. (J. Mol. Biol., 262, 732-745, 1996).*
Casset et al. (Biochemical and Biophysical Research Communications, 307:198-205, 2003).*
Zhang. J. et al The 2beta2-2beta3 loop of anthrax protective antigen contains a dominant neutralizing epitope, Biochemical & Biophysical Research Communications, Mar. 24, 2006 vol. 341. No. 4 pp. 1164-1171 ISSN 0006-291X.
Aziz, M.A. and Bhatnagar r. Accession No. AA698414 NCBI protein database [online], Nov. 21, 2005 [retrieved on Sep. 6, 2007] retrieved from URL:http//www.ncbi.nlm.nih.gov/entrez/viwer.fcgi?db=protein&id51235130.
Gubbins, M. J. et al "Production and characterization of neutralizing monoclonal antibodies that recognize an epitope in domain 2 of *Bacillus anthracis* protective antigen" FEMS Immonol Med Microbiol Aug. 2006 vol. 47 No. 3 pp. 435-443 ISSN 0928-8244.
Mohamed, N. et al A high-affinity monoclonal antibody to anthrax protective antigen passively protects rabbits before and after aerosolized *Bacillus anthracis* spore challenge; Infection & Immunity Feb. 2005 vol. 73 n. 2 pp. 795-802 ISSN 0019-9567.
Little S.F. et al "Production and characterizationo f monoclonal antibodies to the protectiev antigen component of *Bacillus anthracis* toxin" Infectin & Immunity Jul. 1988 vol. 56 No. 7 pp. 1807-1813 ISSN 0019-9567.

* cited by examiner

*Primary Examiner* — Vanessa L. Ford
*Assistant Examiner* — Lakia Tongue
(74) *Attorney, Agent, or Firm* — Michael R. William; Ade & Company Inc

(57) ABSTRACT

The characterization and isolation of F20G75, F20G76 and F20G77, anti-PA monoclonal antibodies which also have neutralizing activities is described. The monoclonal antibodies may be used as a pharmaceutical composition for treating individuals suspected of or at risk of or having a *Bacillus anthracis* infection. The monoclonal antibodies bind to a specific region comprising amino acids 311-316 of PA, ASFFDI or a larger fragment comprising amino acids 301-330 of PA, SEVHGNAEVHASFFDIGSSVSAGFSNSNSS. Vaccines comprising these peptides may be used to immunize individuals against *Bacillus anthracis* infection.

3 Claims, 2 Drawing Sheets

Figures 1, 2:
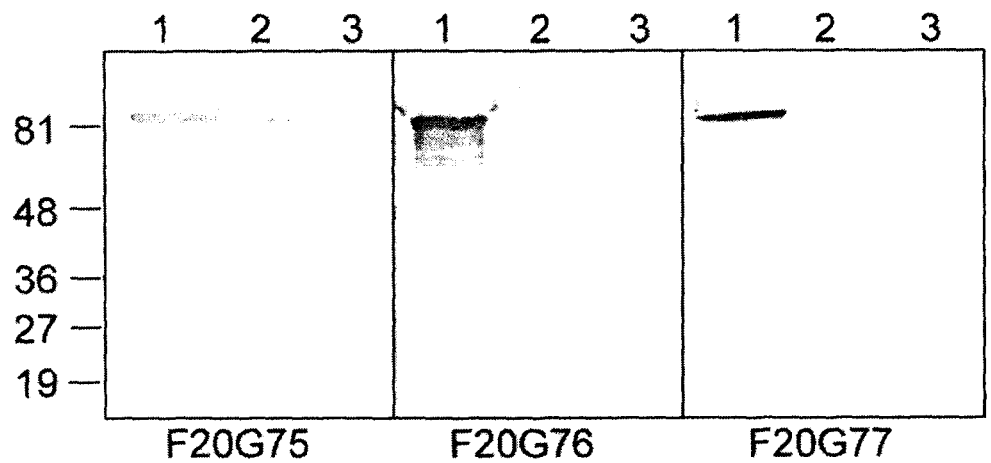

$^{301}$SEVHGNAEVHASFFD
   NAEVHASFFDIGGSV
      ASFFDIGGSVSAGFS$^{325}$

SEQUENCE LISTING

<160> NUMBER OF SEQ ID NOS: 20

<210> SEQ ID NO 1
<211> LENGTH: 30
<212> TYPE: PRT
<213> ORGANISM: Bacillus anthracis
<220> FEATURE:
<221> NAME/KEY: MISC_FEATURE
<222> LOCATION: (1)..(30)
<223> OTHER INFORMATION: amino acids 301-330 of PA protein

<400> SEQUENCE: 1

Ser Glu Val His Gly Asn Ala Glu Val His Ala Ser Phe Phe Asp Ile
1               5                   10                  15

Gly Ser Ser Val Ser Ala Gly Phe Ser Asn Ser Asn Ser Ser
            20                  25                  30

<210> SEQ ID NO 2
<211> LENGTH: 6
<212> TYPE: PRT
<213> ORGANISM: Bacillus anthracis
<220> FEATURE:
<221> NAME/KEY: MISC_FEATURE
<222> LOCATION: (1)..(6)
<223> OTHER INFORMATION: amino acids 311-316 of PA protein

<400> SEQUENCE: 2

Ala Ser Phe Phe Asp Ile
1               5

<210> SEQ ID NO 3
<211> LENGTH: 30
<212> TYPE: PRT
<213> ORGANISM: artificial
<220> FEATURE:
<223> OTHER INFORMATION: variant of seq ID No. 1, based on amino acids
      301-330 of PA protein

<400> SEQUENCE: 3

Ser Glu Val His Gly Asn Ala Glu Val Ala Ala Ser Phe Phe Asp Ile
1               5                   10                  15

Gly Ser Ser Val Ser Ala Gly Phe Ser Asn Ser Asn Ser Ser
            20                  25                  30

<210> SEQ ID NO 4
<211> LENGTH: 30
<212> TYPE: PRT
<213> ORGANISM: artificial
<220> FEATURE:
<223> OTHER INFORMATION: variant of SEQ ID No. 1, based on amino acids
      301-330 of PA peptide

<400> SEQUENCE: 4

Ser Glu Val His Gly Asn Ala Glu Val His Ala Ser Glu Glu Asp Ile
1               5                   10                  15

Gly Ser Ser Val Ser Ala Gly Phe Ser Asn Ser Asn Ser Ser
            20                  25                  30

<210> SEQ ID NO 5
<211> LENGTH: 30
<212> TYPE: PRT
<213> ORGANISM: artificial
<220> FEATURE:
<223> OTHER INFORMATION: variant of SEQ ID No. 1, based on amino acids
      301-330 of PA

```
<400> SEQUENCE: 5

Ser Glu Val His Gly Asn Ala Glu Val Ala Ala Ser Glu Glu Asp Ile
1               5                   10                  15

Gly Ser Ser Val Ser Ala Gly Phe Ser Asn Ser Asn Ser Ser
            20                  25                  30

<210> SEQ ID NO 6
<211> LENGTH: 6
<212> TYPE: PRT
<213> ORGANISM: artificial
<220> FEATURE:
<223> OTHER INFORMATION: variant of SEQ ID No. 2, based on amino acids
      311-316 of PA protein

<400> SEQUENCE: 6

Ala Ser Glu Glu Asp Ile
1               5

<210> SEQ ID NO 7
<211> LENGTH: 30
<212> TYPE: PRT
<213> ORGANISM: artificial
<220> FEATURE:
<223> OTHER INFORMATION: variant of SEQ ID No. 1, based on amino acids
      301-330 of PA protein

<400> SEQUENCE: 7

Ser Glu Val His Gly Asn Ala Glu Val His Ala Ser Phe Phe Asp Ile
1               5                   10                  15

Gly Gly Ser Val Ser Ala Gly Phe Ser Asn Ser Asn Ser Ser
            20                  25                  30

<210> SEQ ID NO 8
<211> LENGTH: 20
<212> TYPE: PRT
<213> ORGANISM: artificial
<220> FEATURE:
<223> OTHER INFORMATION: derived from amino acids 306-325 of PA protein

<400> SEQUENCE: 8

Asn Ala Glu Val His Ala Ser Phe Phe Asp Ile Gly Gly Ser Val Ser
1               5                   10                  15

Ala Gly Phe Ser
            20

<210> SEQ ID NO 9
<211> LENGTH: 396
<212> TYPE: DNA
<213> ORGANISM: mouse
<220> FEATURE:
<221> NAME/KEY: misc_feature
<222> LOCATION: (1)..(396)
<223> OTHER INFORMATION: F20G75 light chain variable region

<400> SEQUENCE: 9
atgttctgga ttcctgcttc cagcagtgat gttttgatga cccaaactcc actctccctg    60
cctgtcagtc ttggagatca agcctccatc tcttgtagat ctagtcagag cattatacat   120
agtaatggag acacctttttt agaatggttc ctgcagaaaac caggccagtc tccaaagctc   180
ctgatctaca aagtttccaa ccgattttct ggggtcccag acaggttcag tggcagtgga   240
tcagggacag atttcacact caagatcagc agagtggagg ctgaggatct gggagtttat   300
tactgctttc aaggttcaca tgttccgctc acgttcggtg ctgggaccaa gctggagctg   360
aaacgggctg atgctgcacc aactgtatcc aagggc                              396
```

<210> SEQ ID NO 10
<211> LENGTH: 132
<212> TYPE: PRT
<213> ORGANISM: mouse
<220> FEATURE:
<221> NAME/KEY: MISC_FEATURE
<222> LOCATION: (1)..(132)
<223> OTHER INFORMATION: F20G75 light chain variable region amino acid sequence

<400> SEQUENCE: 10

Met Phe Trp Ile Pro Ala Ser Ser Asp Val Leu Met Thr Gln Thr
1               5                   10                  15

Pro Leu Ser Leu Pro Val Ser Leu Gly Asp Gln Ala Ser Ile Ser Cys
            20                  25                  30

Arg Ser Ser Gln Ser Ile Ile His Ser Asn Gly Asp Thr Phe Leu Glu
        35                  40                  45

Trp Phe Leu Gln Lys Pro Gly Gln Ser Pro Lys Leu Leu Ile Tyr Lys
    50                  55                  60

Val Ser Asn Arg Phe Ser Gly Val Pro Asp Arg Phe Ser Gly Ser Gly
65                  70                  75                  80

Ser Gly Thr Asp Phe Thr Leu Lys Ile Ser Arg Val Glu Ala Glu Asp
                85                  90                  95

Leu Gly Val Tyr Tyr Cys Phe Gln Gly Ser His Val Pro Leu Thr Phe
            100                 105                 110

Gly Ala Gly Thr Lys Leu Glu Leu Lys Arg Ala Asp Ala Ala Pro Thr
        115                 120                 125

Val Ser Lys Gly
    130

<210> SEQ ID NO 11
<211> LENGTH: 372
<212> TYPE: DNA
<213> ORGANISM: mouse
<220> FEATURE:
<221> NAME/KEY: misc_feature
<222> LOCATION: (1)..(372)
<223> OTHER INFORMATION: F20G76 light chain variable region

<400> SEQUENCE: 11
gagctcgtga tgacccagtc tccactctcc ctgcctgtca gtcttggaga tcaagcctcc      60
atctcttgta gatctagtca gagcattata catagtaatg agacaccttt tttagaatgg     120
ttcctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaacggg ctgatgctgc accaactgta     360
aagggcgaat tc                                                         372

<210> SEQ ID NO 12
<211> LENGTH: 124
<212> TYPE: PRT
<213> ORGANISM: mouse
<220> FEATURE:
<221> NAME/KEY: MISC_FEATURE
<222> LOCATION: (1)..(124)
<223> OTHER INFORMATION: F20G76 light chain variable region

<400> SEQUENCE: 12

Glu Leu Val Met Thr Gln Ser Pro Leu Ser Leu Pro Val Ser Leu Gly

```
                1               5                  10                 15
Asp Gln Ala Ser Ile Ser Cys Arg Ser Ser Gln Ser Ile Ile His Ser
                    20                  25                  30

Asn Gly Asp Thr Phe Leu Glu Trp Phe Leu Gln Lys Pro Gly Gln Ser
                35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Leu Gly Val Tyr Tyr Cys Gln Gly
                    85                  90                  95

Ser His Val Pro Leu Thr Phe Gly Ala Gly Thr Lys Leu Glu Leu Lys
                100                 105                 110

Arg Ala Asp Ala Ala Pro Thr Val Lys Gly Glu Phe
                115                 120
```

```
<210> SEQ ID NO 13
<211> LENGTH: 730
<212> TYPE: DNA
<213> ORGANISM: mouse
<220> FEATURE:
<221> NAME/KEY: misc_feature
<222> LOCATION: (1)..(730)
<223> OTHER INFORMATION: F20G77 light chain variable region

<400> SEQUENCE: 13
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgtagat ctagtcagag cattatacat agtaatggag acacctttt agaatggttc   180 ctgcagaaac caggccagtc tccaaagctc ctgatctaca agtttccaa ccgattttct   240 ggggtcccag acaggttcag tggcagtgga tcaggacag atttcacact caagatcagc   300
agagtggagg ctgaggatct gggagtttat tactgctttc aaggttcaca tgttccgctc   360
acgttcggtg ctgggaccaa gctggagctg aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600 agcacccctca cgttgaccaa ggacgagtat gaacgacata cagctatac ctgtgaggcc   660 actcacaaga catcaacttc acccattgtc aagagcttca caggaatga gtgttaattc   720 tagacggcgc                                                           730
```

```
<210> SEQ ID NO 14
<211> LENGTH: 134
<212> TYPE: PRT
<213> ORGANISM: mouse
<220> FEATURE:
<221> NAME/KEY: MISC_FEATURE
<222> LOCATION: (1)..(134)
<223> OTHER INFORMATION: F20G77 light chain variable region

<400> SEQUENCE: 14

Asn Ser Pro Phe Glu Val Gln Leu Glu Glu Ser Gly Pro Glu Leu Val
 1               5                  10                  15

Ser Pro Gly Val Ser Val Lys Ile Ser Cys Glu Gly Ser Gly Tyr Thr
                20                  25                  30

Phe Thr Asp Tyr Ala Met His Trp Val Lys Gln Ser His Ala Arg Gly
```

```
                    35                  40                  45
Leu Glu Trp Ile Gly Val Ile Gly Ser Tyr Ser Gly Asn Ala His His
    50                  55                  60

Asn Leu Asn Phe Lys Asp Lys Ala Thr Met Thr Val Asp Lys Ser Ser
65                  70                  75                  80

Ser Thr Ala Tyr Met Glu Leu Ala Arg Leu Thr Ser Asp Asp Ser Ala
                85                  90                  95

Ile Tyr Tyr Cys Ala Tyr Thr Thr Leu Trp Ala Thr Leu Gly
                100                 105                 110

Leu Pro Glu Ala Thr Gly Leu Trp Ser Leu Ser Leu Gln Pro Lys Arg
            115                 120                 125

His Pro His Leu Arg Ala
            130

<210> SEQ ID NO 15
<211> LENGTH: 367
<212> TYPE: DNA
<213> ORGANISM: mouse
<220> FEATURE:
<221> NAME/KEY: misc_feature
<222> LOCATION: (1)..(367)
<223> OTHER INFORMATION: F20G75 heavy chain variable region sequence

<400> SEQUENCE: 15 gcccctttgag gtgcagctgg aggagtctgg gggagactta gtgaagcctg gagggtccct       60
aaaactctcc tgtgcagcct ctggattcac tttcagtgac tatggcatgt cttggattcg      120
ccagactcca gacaggaggc tggagtgggt cgcaaccatt agtactggtg gtacttacac      180
ctattatcta gacagtgtga agggcgatt caccatctcc agagacaatg ccaagaacac      240
cctgtaccta caaatgaaca gtctgaagtc tgaggacaca gccatgtatt actgttcgaa      300
cgacgacctg ggtcaaggaa cctcagtcac agtctcctca gccaaaacga cacccccatc      360
taagggc                                                                367

<210> SEQ ID NO 16
<211> LENGTH: 122
<212> TYPE: PRT
<213> ORGANISM: mouse
<220> FEATURE:
<221> NAME/KEY: MISC_FEATURE
<222> LOCATION: (1)..(122)
<223> OTHER INFORMATION: F20G75 heavy chain variable region

<400> SEQUENCE: 16

Pro Phe Glu Val Gln Leu Glu Glu Ser Gly Gly Asp Leu Val Lys Pro
1               5                   10                  15

Gly Gly Ser Leu Lys Leu Ser Cys Ala Ala Ser Gly Phe Thr Phe Ser
            20                  25                  30

Asp Tyr Gly Met Ser Trp Ile Arg Gln Thr Pro Asp Arg Arg Leu Glu
        35                  40                  45

Trp Val Ala Thr Ile Ser Thr Gly Gly Thr Tyr Thr Tyr Tyr Leu Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Ser Glu Asp Thr Ala Met Tyr
                85                  90                  95

Tyr Cys Ser Asn Asp Asp Leu Gly Gln Gly Thr Ser Val Thr Val Ser
                100                 105                 110

Ser Ala Lys Thr Thr Pro Pro Ser Lys Gly
```

<210> SEQ ID NO 17
<211> LENGTH: 376
<212> TYPE: DNA
<213> ORGANISM: mouse
<220> FEATURE:
<221> NAME/KEY: misc_feature
<222> LOCATION: (1)..(376)
<223> OTHER INFORMATION: F20G76 heavy chain variable region

<400> SEQUENCE: 17

```
gcccttgag gtgcagctgg aggagtctgg acctgagctg gtgaagcctg gggcttcagt      60
gaaggtatcc tgcaaggctt ctggttactc attcactgac tacaacatgt actgggtgaa     120
gcagagccat ggaacgagcc ttgagtggat tggcgttatt gatcctaaca atggtgttac     180
tagctacaac cagaagttca aggacaaggc cacattgact gctgacaagt cctccagtac     240
agccttcatg catctcaaca gcctgacatc tgaggactct gcagtctatt attgttcaag     300
agggggtctt gactactggg gccagggcac cactctcaca gtctcctcag ccaaaacgac     360
accccatct aagggc                                                      376
```

<210> SEQ ID NO 18
<211> LENGTH: 125
<212> TYPE: PRT
<213> ORGANISM: mouse
<220> FEATURE:
<221> NAME/KEY: MISC_FEATURE
<222> LOCATION: (1)..(125)
<223> OTHER INFORMATION: F20G76 heavy chain variable region sequence

<400> SEQUENCE: 18

```
Pro Phe Glu Val Gln Leu Glu Glu Ser Gly Pro Glu Leu Val Lys Pro
1               5                   10                  15
Gly Ala Ser Val Lys Val Ser Cys Lys Ala Ser Gly Tyr Ser Phe Thr
            20                  25                  30
Asp Tyr Asn Met Tyr Trp Val Lys Gln Ser His Gly Thr Ser Leu Glu
        35                  40                  45
Trp Ile Gly Val Ile Asp Pro Asn Asn Gly Val Thr Ser Tyr Asn Gln
    50                  55                  60
Lys Phe Lys Asp Lys Ala Thr Leu Thr Ala Asp Lys Ser Ser Ser Thr
65                  70                  75                  80
Ala Phe Met His Leu Asn Ser Leu Thr Ser Glu Asp Ser Ala Val Tyr
                85                  90                  95
Tyr Cys Ser Arg Gly Gly Leu Asp Tyr Trp Gly Gln Gly Thr Thr Leu
            100                 105                 110
Thr Val Ser Ser Ala Lys Thr Thr Pro Pro Ser Lys Gly
        115                 120                 125
```

<210> SEQ ID NO 19
<211> LENGTH: 402
<212> TYPE: DNA
<213> ORGANISM: mouse
<220> FEATURE:
<221> NAME/KEY: misc_feature
<222> LOCATION: (1)..(402)
<223> OTHER INFORMATION: F20G77 heavy chain variable region

<400> SEQUENCE: 19

```
aattcgccct tgaggtgca gctggaggag tctgggcctg agctggtgag tcctggggtc      60
tcagtgaaga tttcctgcga gggttccggc tacacattca ctgattatgc tatgcactgg    120
```

-continued

```
gtgaaacaga gtcatgcaag gggtctagag tggattggag ttattggttc ttactctggt    180
aatgcacacc acaacctgaa ctttaaggac aaggccacaa tgactgtaga caagtcctcc    240
agcacagcct atatggaact tgctagattg acatctgacg attctgccat ctattactgt    300
gcatatactc ggacgacact ttgggctacg ttgggtctgc ctgaggccac gggactctgg    360
tcactgtctc tgcagccaaa acgacacccc catctaaggg cg                      402
```

<210> SEQ ID NO 20
<211> LENGTH: 134
<212> TYPE: PRT
<213> ORGANISM: mouse
<220> FEATURE:
<221> NAME/KEY: MISC_FEATURE
<223> OTHER INFORMATION: F20G77 heavy chain variable region sequence

<400> SEQUENCE: 20

```
Asn Ser Pro Phe Glu Val Gln Leu Glu Glu Ser Gly Pro Glu Leu Val
1               5                   10                  15

Ser Pro Gly Val Ser Val Lys Ile Ser Cys Glu Gly Ser Gly Tyr Thr
            20                  25                  30

Phe Thr Asp Tyr Ala Met His Trp Val Lys Gln Ser His Ala Arg Gly
        35                  40                  45

Leu Glu Trp Ile Gly Val Ile Gly Ser Tyr Ser Gly Asn Ala His His
    50                  55                  60

Asn Leu Asn Phe Lys Asp Lys Ala Thr Met Thr Val Asp Lys Ser Ser
65                  70                  75                  80

Ser Thr Ala Tyr Met Glu Leu Ala Arg Leu Thr Ser Asp Asp Ser Ala
                85                  90                  95

Ile Tyr Tyr Cys Ala Tyr Thr Arg Thr Thr Leu Trp Ala Thr Leu Gly
            100                 105                 110

Leu Pro Glu Ala Thr Gly Leu Trp Ser Leu Ser Leu Gln Pro Lys Arg
        115                 120                 125

His Pro His Leu Arg Ala
    130
```

MONOCLONAL ANTIBODIES TO ANTHRAX PROTECTIVE ANTIGEN

PRIOR APPLICATION INFORMATION

This application claims the benefit of U.S. Provisional Application 60/800,831, filed May 17, 2006.

FIELD OF THE INVENTION

The invention relates to vaccines for *Bacillus anthracis* infections.

BACKGROUND OF THE INVENTION

Anthrax is a well-known infectious disease caused by a Gram-positive bacterium, *Bacillus anthracis*. There are three types of anthrax infections: cutaneous, gastrointestinal and inhalation. Inhalation anthrax generally occurs after an incubation time of 1-6 days. After the incubation period, a non-specific flu-like illness ensues for 1-3 days followed by a brief intervening period of improvement. Unfortunately, rapid deterioration follows and death is universal in untreated cases.

Airborne anthrax has long been concerned a major bioterror threat and it has recently been shown that anthrax can be aerosolized and transmitted by mail.

The causative agent of anthrax, *Bacillus anthracis*, expresses three major extracellular toxin protein components, encoded on its large pXO1 plasmid (Okinaka et al., 1999). Protective antigen (PA) combines with either lethal factor (LF) or edema factor (EF) to form a functional binary toxin (reviewed in Abrami et al., 2005). PA in combination with LF causes death in experimental animals (Smith and Keppie, 1954, Nature 173: 869-870) while PA in combination with EF causes edema in the skin of experimental animals (Stanley and Smith, 1961, J Gen Microbiol 26: 49-66). While none of the proteins is individually toxic, PA combines with either LF or EF to form one of two binary toxins. PA binds to one of two cellular receptors, TEM8 (Bradley et al., 2001; Liu and Leppla, 2003) or CMG2 (Scobie et al., 2003). Upon receptor binding, the 83 kDa PA (PA83) is cleaved at a specific sequence by furin or a furin-like protease, releasing a 20 kDa N-terminal fragment (PA20) while leaving a 63 kDa C-terminal fragment (PA63) bound to the receptor (Singh et al., 1989; Molloy et al., 1992). An LF binding site on PA63 is simultaneously exposed via this cleavage event (Novak et al., 1992). Spontaneous heptamerization of the PA:receptor complex occurs (Milne et al., 1994), allowing competitive, high affinity binding by EF or LF (Cunningham et al., 2002; Mogridge et al., 2002), followed by internalization of the toxin:receptor complex via clathrin-mediated endocytosis (Abrami et al., 2003). Acidification of the endosome produces structural rearrangements in the PA prepore heptamer, leading to pore formation and membrane insertion (Lacy et al., 2004; Santelli et al., 2004), and subsequent release of LF and/or EF into the cytosol (reviewed in Abrami et al., 2005).

PA is the primary antigenic determinant in currently licensed human anthrax vaccines (Turnbull et al., 1986; Leppla et al., 2002; Baillie et al., 2004; Adams et al., 2005). Several recent model studies demonstrate that a strong humoral response to PA contributes to a protective immune response to anthrax (Miller et al., 1998; Pitt et al., 2001; Reuveny et al., 2001; Little et al., 2004), and several regions that serve as targets for neutralizing monoclonal antibodies have been identified (Little et al., 1996; Brossier et al., 2004). The mature 735 amino acid PA protein (GenBank accession number AAT98414) contains four distinct functional domains (Petosa et al., 1997). Domain 1 (residues 1-258) functions in oligomerization of PA and binding to LF and EF (Chauhan & Bhatnagar, 2002; Cunningham et al., 2002; Lacy et al., 2004), and contains the sequence $^{164}$RKKR$^{167}$, which serves as the furin cleavage site (Singh et al., 1989; Molloy et al., 1992). Domain 2 (residues 259-487) functions in pore formation, heptamerization, membrane insertion, and translocation of EF and LF (Benson et al., 1998; Miller et al., 1999; Singh et al., 1994). Domain 3 (residues 488-595) functions in oligomerization (Mogridge et al., 2001), while domain 4 (residue 596-735) functions in binding the cellular receptor (Singh et al., 1991; Varughese et al., 1999; Santelli et al., 2004).

Multiple MAbs that target different regions of PA and neutralize LeTx in vitro have been previously characterized. Several MAbs target epitopes in domain 4, and neutralize the toxin by preventing PA from binding to its cellular receptor (Little et al., 1988; Little et al., 1996; Brossier et al., 2004). Other MAbs target epitopes in regions spanning the interfaces between domains 1 and 2 and domains 3 and 4, and prevent LF from interacting with PA at the cell surface (Little et al., 1996), or target epitopes in domain 2, preventing cleavage of PA83 to PA63 (Brossier et al., 2004). To identify unique neutralizing epitopes in PA, MAbs were raised in mice using whole rPA as the immunogen, and their affinities and epitope specificities were characterized.

PCT application WO 02/100340 teaches a vaccine comprising recombinant PA which may be combined with LFn, a Lethal Factor deletion which has the C-terminal 47 amino acids removed, thereby eliminating the lethal toxin forming activity.

Published patent application US 2004/0028695 teaches an expression vector for a "27 kDa N-terminal PA deletion mutant PA27. This mutant contains amino acid 498-735 of PA and the purpose of this mutant is to create a smallest PA deletion mutant to be used as an effective antigen." In one embodiment of the invention, a fusion protein comprising the N-terminal domain 1 of LF and the C-terminal domains 3 and 4 of PA are fused, with domain 3 of PA acting as "a spacer region . . . to keep the correct folding structures of the other two domains from LF and PA".

These vaccines are based on the observation that the protective efficacy of PA is greatly increased if small quantities of LF or EF are incorporated into the vaccine (Pezard et al., 1995, Infect. Immun. 63: 1369-1372). However, it is believed that this also happens to be the primary cause of toxigenicity and reactogenicity of the vaccines.

Published patent application US 2004/0009945 teaches an anthrax vaccine wherein the PA coding sequence is inserted into a VEE virus vector in place of VEE virus structural genes.

PCT application WO 03/048390 teaches an anthrax vaccine which comprises PA, LF and EF together wherein these proteins have been rendered non-toxic by introducing mutations which affect the biological activity of the proteins without affecting their structure or immunogenicity.

Clearly, there remains a need for an anthrax vaccine which has a well defined composition and has minimal, if any, side effects.

SUMMARY OF THE INVENTION

According to a first aspect of the invention, there is provided an anti-*Bacillus anthracis* antibody comprising an amino acid sequence as set forth in any one of SEQ ID No. 10, 12, 14, 16, 18 or 20.

According to a second aspect of the invention, there is provided a pharmaceutical composition comprising an antibody as described above and a suitable excipient.

According to a fourth aspect of the invention, there is provided a pharmaceutical composition comprising a chimeric antibody as described above and a suitable excipient.

According to a fifth aspect of the invention, there is provided a *Bacillus anthracis* neutralizing monoclonal antibody selected from the group consisting of F20G75, F20G76 and F20G77.

According to a sixth aspect of the invention, there is provided a pharmaceutical composition comprising a *Bacillus anthracis* neutralizing monoclonal antibody selected from the group consisting of F20G75, F20G76, F20G77 and combinations thereof and a suitable excipient.

According to a seventh aspect of the invention, there is provided a method of preventing toxicity associated with the toxins of *Bacillus anthracis* toxicity in an individual comprising administering to said individual an effective amount of a pharmaceutical composition comprising a *Bacillus anthracis* neutralizing monoclonal antibody selected from the group consisting of F20G75, F20G76, F20G77 and combinations thereof and a suitable excipient According to an eighth aspect of the invention method of preventing toxicity associated with the toxins of *Bacillus anthracis* toxicity in an individual comprising administering to said individual an effective amount of a pharmaceutical composition as described above.

According to a ninth aspect of the invention, there is provided an isolated peptide comprising at least 6 consecutive amino acids of any one of SEQ ID No. 1-9.

BRIEF DESCRIPTION OF THE FIGURES AND TABLES

FIG. 1. Western immunoblot analysis probing specificity and MAb reactivity for rPA. Samples of 2 µg of protein were heat denatured and subjected to SDS-PAGE, followed by electrophoretic transfer to nitrocellulose membranes. The blots were probed with MAbs F20G75, F20G76, or F20G77, as indicated below each panel. Lane 1, rPA; lane 2, rLF; lane 3, BSA. Protein size markers (kDa) are shown on the left of the figure.

FIG. 2. PA domain 2 peptide sequences recognized by MAbs F20G75, F20G76, and F20G77, as determined by pin-peptide epitope mapping (described in Section 2). Amino acid numbering is taken from the mature PA protein (GenBank accession number AAT98414; first line is amino acids 1-15 of SEQ ID NO:7; second line is amino acids 6-20 of SEQ ID NO:7; and third line is amino acids 11-25 of SEQ ID NO:7). Residues common to all three peptides are in bold text (SEQ ID NO:6).

Figure 3:
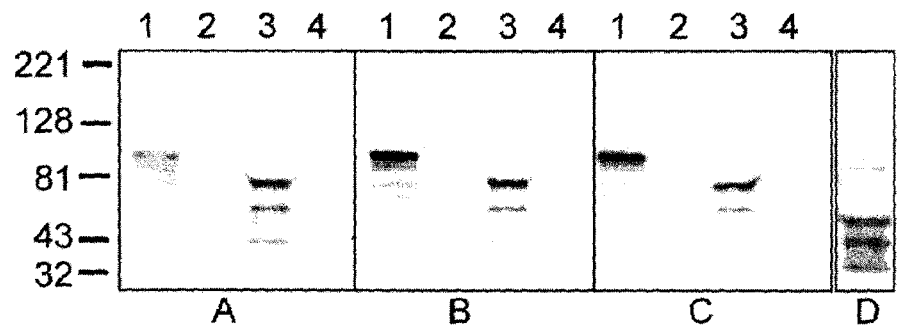

FIG. 3. Western immunoblot analysis probing MAb reactivity with trypsin and chymotrypsin digests of rPA. Samples of 2 µg of rPA were subjected to digestion by 40 ng of trypsin or chymotrypsin for 10 minutes on ice, followed by the addition of inhibitor. The digests, and samples of 2 µg of undigested rPA, were then heat denatured and subjected to SDS-PAGE followed by electrophoretic transfer to nitrocellulose membranes. The blots were probed with MAbs F20G75 (A), F20G76 (B), or F20G77 (C). Lane 1: rPA, lane 2: BSA, lane 3: trypsin digested rPA, lane 4: chymotrypsin digested rPA. To confirm that chymotrypsin digestion was effective, the same blots were washed and then re-probed with PA-specific rabbit polyclonal antiserum. A representative example of chymotrypsin digested rPA probed with this antiserum is shown in panel D. Size markers (kDa) are shown on the left of the figure.

Figure 4:
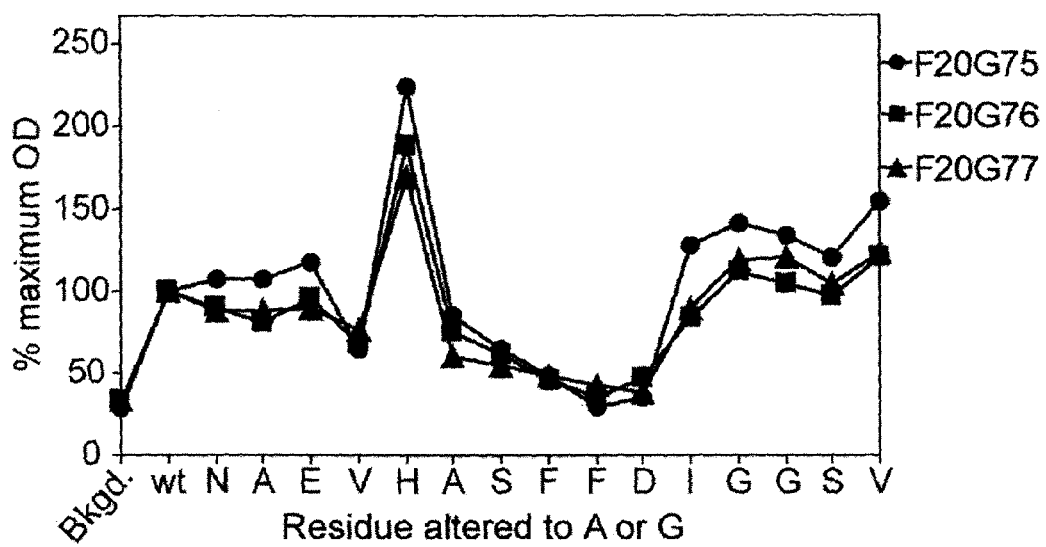

FIG. 4. Pin-peptide epitope mapping to determine critical residues in the epitope extending from N306 to V320 in rPA. Synthetic peptides on a solid support matrix were synthesized such that every residue extending from N306 to V320 was altered in turn to Ala (or Gly in the case where an Ala was already present in the epitope) and their reactivities with MAbs F20G75, F20G76, and F20G77 were assessed via ELISA. The background OD405 value was determined from reactivity of the MAbs with unrelated peptide sequences present on the same pin-peptide block. The OD reading for MAb binding to the "wild-type" peptide (no changes to any amino acid within the epitope) was considered the baseline maximum binding level, to which the OD readings for MAbs binding to the altered peptides were compared as an indication of binding efficiency (% maximum OD=(OD of altered peptide/OD of unaltered peptide)×100). The assay was performed twice for each MAb, and the average value of two experiments is plotted in the graph.

Table 1. Endpoint ELISA titres and affinity of the rPA-specific MAbs.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the characterization and isolation of a number of anti-PA monoclonal antibodies that also have neutralizing activities. Specifically, the monoclonal antibodies are designated as F20G75 (light chain nucleotide sequence is SEQ ID No. 9, light chain amino acid sequence is SEQ ID No. 10; heavy chain nucleotide sequence is SEQ ID No. 15, heavy chain amino acid sequence is SEQ ID No. 16), F20G76 (light chain nucleotide sequence is SEQ ID No. 11, light chain amino acid sequence is SEQ ID No. 12; heavy chain nucleotide sequence is SEQ ID No. 17, heavy chain amino acid sequence is SEQ ID No. 18), and F20G77 (light chain nucleotide sequence is SEQ ID No. 13, light chain amino acid sequence is SEQ ID No. 14; heavy chain nucleotide sequence is SEQ ID No. 19, heavy chain amino acid sequence is SEQ ID No. 20).

Specifically, as will be appreciated by one of skill in the art, the amino acid sequences described above correspond to the variable regions of the monoclonal antibodies. Accordingly, in some embodiments of the invention, there are provided chimeric antibodies comprising an amino acid sequence as set forth in SEQ ID 10, 12 or 14 (F20G75, F20G76 and F20G77 light chain variable region respectively) or chimer antibodies comprising an amino acid sequence as set forth in SEQ ID No. 16, 18 or 20 (F20G75, F20G76 and F20G77 heavy chain variable region respectively). As will be appreciated by one of skill in the art, may be combined for example fused either chemically or genetically to corresponding human constant regions, for example, human IgG1 and IgG2.

In a preferred embodiment of the invention, there are provided chimeric antibodies comprising a light chain amino acid sequence as set forth in SEQ ID 10, 12 or 14 (F20G75, F20G76 and F20G77 light chain variable region respectively)

and a heavy chain amino acid sequence as set forth in SEQ ID No. 16, 18 or 20 (F20G75, F20G76 and F20G77 heavy chain variable region respectively). As will be appreciated by one of skill in the art, may be combined for example fused either chemically or genetically to corresponding human constant regions, for example, human IgG1 and IgG2.

In a further preferred embodiment of the invention, there are provided chimeric antibodies comprising a light chain amino acid sequence as set forth in SEQ ID 10 and a heavy chain amino acid sequence as set forth in SEQ ID No. 16 (light and heavy variable regions from F20G72); a light chain amino acid sequence as set forth in SEQ ID No. 12 and a heavy chain amino acid sequence as set forth in SEQ ID No. 18 (F20G76 light and heavy chains variable regions); or a light chain amino acid sequence as set forth in SEQ ID No. 14 and a heavy chain amino acid sequence as set forth in SEQ ID No. 20 (F20G77 light and heavy chain variable regions) As will be appreciated by one of skill in the art, may be combined for example fused either chemically or genetically to corresponding human constant regions, for example, human IgG1 and IgG2.

As will be appreciated by one of skill in the art, the monoclonal antibodies or chimeric antibodies prepared as described above, either individually or in any various combination may be used as a pharmaceutical composition for treating individuals suspected of or at risk of or having a *Bacillus anthracis* infection when combined with a suitable excipient as known in the art and as discussed herein.

In other embodiments, an antibody selected from the group consisting of F20G75, F20G76, F20G77 and humanized or chimeric antibodies derived therefrom as described above are used, for example, as a standard, to screen a sample, for example, human sera samples for the presence of *Bacillus anthracis* or serum antibodies specific for *Bacillus anthracis*. As will be appreciated by one of skill in the art, the use of antibodies to detect the presence of antigenic determinants within a sample is well-established and may be done by a variety of means. In general however, the process involves the incubation of a sample of interest with an antibody selected from the group consisting of F20G75, F20G76, F20G77 and humanized or chimeric antibodies derived therefrom as described above under conditions suitable for antibody-antigen interactions; and detecting if an antibody-antigen interaction has occurred.

Suitable conditions may include for example incubation at a temperature within a certain range for a certain period of time in the presence of additional chemicals that either promote specific binding or impair non-specific binding. Such conditions are well known to one of skill in the art. It is further noted that means for detecting antibody binding are numerous and are well known in the art.

As will be appreciated by one of skill in the art, the nucleotide sequences encoding the light chains and/or heavy chains of F20G75, F20G76 and/or F20G77 may be operably linked to a suitable promoter such as a known promoter typically used in a suitable expression system for expression of the F20G75 light chain (SEQ ID No. 10) or heavy chain (SEQ ID No. 16), the F20G76 light chain (SEQ ID No. 12) or heavy chain (SEQ ID No. 18) or the F20G77 light chain (SEQ ID No. 14) or heavy chain (SEQ ID No. 20). Alternatively, nucleotide sequences deduced from the corresponding amino acid sequences may be used or the peptides may be synthesized artificially.

In other embodiments, the light chains and/or heavy chains as described above are used in the manufacture of humanized or chimeric antibodies using means known in the art. As is known to one of skill in the art, this process involves replacement of the non-human immunoglobulin sequences with human sequences, thereby increasing tolerance of the antibody(s) by a human immune system. Accordingly, in some embodiments of the invention, there is provided a method of generating a humanized or chimeric anti-Anthrax antibody comprising providing As discussed below, the above-described monoclonal antibodies bind to a specific region comprising amino acids 311-316 of PA, ASFFDI (SEQ ID NO: 2) or a larger fragment comprising amino acids 301-330 of PA,

```
SEVHGNAEVHASFFDIGSSVSAGFSNSNSS.    (SEQ ID NO. 1)
```

As will be appreciated by one of skill in the art, vaccines comprising or consisting of at least 6, at least 7, at least 8, at least 9, at least 10, at least 11 or at least 12 consecutive amino acids of

```
SEVHGNAEVHASFFDIGSSVSAGFSNSNSS     (SEQ ID No. 1)
or
SEVHGNAEVAASFFDIGSSVSAGFSNSNSS     (SEQ ID No. 3)
or
SEVHGNAEVHASEEDIGSSVSAGFSNSNSS     (SEQ ID No. 4)
or
SEVHGNAEVAASEEDIGSSVSAGFSNSNSS,    (SEQ ID No. 5)
``` or a peptide comprising or consisting of ASFFDI (SEQ ID No. 2) or ASEEDI (SEQ ID No. 6) may be used to immunize individuals at risk of *Bacillus anthracis* infection or individuals in need of or desirous of immunization against a *Bacillus anthracis* infection. Such individuals include for example military personnel or others at risk or believed to be at risk of encountering *Bacillus anthracis*. As will be appreciated by one of skill in the art, a vaccine comprising the above-described peptides may be prepared by a variety of means known in the art. For example, peptides comprising or consisting of SEQ ID NO. 1-6 or variants or fragments thereof may be prepared recombinantly, for example, in bacterial, yeast or baculovirus systems, and purified. In these embodiments, the above-described peptides may be encoded by a cDNA inserted into an appropriate expression vector. In some embodiments, the expression vector may include flanking sequence(s) on either or both sides of the cDNA, which may or may not be native PA sequences. In some embodiments, the cDNA may be embedded within or genetically linked to a suitable carrier protein. These also include fragment(s) of PA expressed by recombinant DNA methods in vitro or in vivo by genetic recombination.

In preferred embodiments, the above described peptides may be synthesized in vitro. These synthetic peptides may be used alone or may be cross-linked or otherwise attached to a suitable carrier protein, thereby producing a fusion protein or recombinant protein, as discussed below. As will be appreciated by one of skill in the art, a significant advantage of the synthetic peptides is that they are in a highly purified form, thereby reducing the risk of side-effects relative to current anthrax vaccines, as discussed above.

It is of note that the use of synthetic peptides or fragments of PA comprising at least 6 consecutive amino acids of SEQ ID No. 1-6 or a variant thereof differs from the use of full-length PA or mutated PA in that by exposing the immune system to this specific epitope, the proportion of neutralizing antibodies produced is much greater compared to use of full-length PA as the antigen. As such, in preferred embodiments, the vaccine may comprise a peptide having at least 6 consecutive amino acids of an amino acid sequence as set forth in any one of SEQ ID No. 1-6 or a variant thereof. As discussed below, the peptides may be administered to individuals at risk of contacting *Bacillus anthracis* or in need of or desirous of immunization against a *Bacillus anthracis* infection in combination with other compounds known in the art of vaccine manufacturing. As discussed above, such peptides may be used in the formation of recombinant or fusion proteins.

It is of note that as discussed herein, the above-described neutralizing antibody or humanized variant thereof, or of other monoclonal antibodies which have similar peptide epitope sub-specificity, may be formulated into a pharmaceutical treatment for providing passive immunity for individuals suspected of or at risk of *Bacillus anthracis* infection comprising a therapeutically effective amount of said antibody. The pharmaceutical preparation may include a suitable excipient or carrier. See, for example, *Remington: The Science and Practice of Pharmacy*, 1995, Gennaro ed. As will be apparent to one knowledgeable in the art, the total dosage will vary according to the weight, health and circumstances of the individual as well as the efficacy of the antibody.

Pharmaceutical compositions comprising the neutralizing monoclonal antibodies F20G75, F20G76, F20G77 or humanized or chimeric antibodies based on or derived from at least one of the F20G75, F20G76 or F20G77 heavy or light variable chains as set forth in SEQ ID Nos. 10, 12, 14, 16, 18 or 20 as described above or combinations thereof may be administered in an effective amount to individuals who have been exposed to or are believed to have been exposed to or are at risk of having been exposed to or at risk of being exposed to *Bacillus anthracis*. Administration of these pharmaceutical compositions will accomplish at least one of the following: slowing disease progression, alleviation of associated symptoms and improved predicted medical outcome.

In other embodiments, there is provided a *Bacillus anthracis* toxin antagonist treatment comprising a peptide made of at least 6 consecutive amino acids of the epitopes identified by mapping said monoclonal antibodies from in-house and USAMRIID sources, discussed herein. As will be appreciated by one of skill in the art, the peptides comprising at least 6, or at least 7, or at least 8 consecutive amino acids of these epitopes will act to inhibit at least one of the following: toxin function, subunit interaction, processing to maturation and binding interactions. As will be apparent to one of skill in the art, such peptides include at least 6, or at least 7, or at least 8 consecutive amino acids of SEVHGNAEVHASFFDIGGS-VSAGFSNSNSS (SEQ ID No. 7) or may comprise or consist of ASFFDI (SEQ ID No. 2) or at least 6 or at least 7 or at least 8 consecutive amino acids from the sequence NAEVHASFF-DIGGSVSAGFS (SEQ ID No. 8). In other embodiments, these peptides include at least 6, at least 7 or at least 8 consecutive amino acids from any one of SEQ ID No. 1, 3, 4, 5 or 7 or may consist or comprise of an amino acid sequence as set forth in SEQ ID Nos. 2 or 6 or variants thereof.

It is of note that It is well known in the art that some modifications and changes can be made in the structure of a polypeptide without substantially altering the biological function of that peptide, to obtain a biologically equivalent polypeptide. In one aspect of the invention, the above-described peptides may include peptides that differ by tolerated amino acid substitutions. The peptides of the present invention also extend to biologically equivalent peptides that differ by tolerated amino acid substitutions. As used herein, the term "tolerated amino acid substitutions" refers to the substitution of one amino acid for another at a given location in the peptide, where the substitution can be made without substantial loss of the relevant function, in this case, the folding of the epitope. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. As discussed herein, a His to Ala mutation, which is not a conservative amino acid substitution, improved monoclonal antibody binding. Similarly, the FF to EE substitution improved peptide solubility as discussed herein.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Len, Ile, Phe, Trp, Pro, Met; acidic: Asp, Glu; basic: Lys, Arg, His; neutral: Gly, Ser, Thr, Cys, Asn, Gln, Tyr. In alternative embodiments, non-conserved amino acid substitutions may be made where an amino acid residue is substituted for another in a different class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. As an example, simply for illustrative purposes and without limiting the invention, a change from His (basic) to Ala (non-polar) or Phe (non-polar) to Glu (acidic) are non-conservative changes.

In summary, using both in-house produced toxin-neutralizing monoclonal antibodies as well as toxin-neutralizing monoclonal antibodies obtained from collaborator(s), we have identified the important epitopes recognized by these toxin-neutralizing monoclonal antibodies.

Based on these potential protective epitope(s) identified by us, newer, better, and well defined subunit anthrax vaccine(s) can be developed for providing individuals with active protection. The objective of these newer subunit vaccine(s) is better immunogenicity as well as less reactogenicity, that is, fewer side effects.

The toxin-neutralizing antibodies may be developed into therapeutics for passive protection.

Synthetic peptides may also indirectly inhibit toxin function and hence may have therapeutic potential. Accordingly, in some embodiments, synthetic peptide vaccines as discussed above are prepared in combination with suitable adjuvants, carrier particles or chemicals, and/or immuno-modulators to booster immune response to the peptides.

Suitable carrier proteins include but are by no means limited to tetanus toxoid, mutant diphtheria toxin, KLH, cholera toxoid or mutant cholera toxin and common plant proteins.

As will be appreciated by one of skill in the art, other suitable adjuvants, such as, for example, but by no means limited to-aluminum or calcium-based compounds such as aluminum hydroxide and calcium or aluminum phosphate particles; MF59, QS-21, AS02, Montanide ISA-51, Montanide ISA-720; ISCOMS; Cationic PLG microparticles; Detox (MPL+CWS): MPL™+*Mycobacterium phlei* cell wall skeleton; MPL™:monophosphoryl lipid A; AGL (RC-529): synthetic acylated mono-saccharide; DC-Chol: lipoidal immunostimulators able to self organize into liposomes; $OM^7$-174; $OM^7$ Triacyl: lipid A derivative; synthetic triacyl pseudo-depeptide; CpG ODN: synthetic oligonucleotides containing immunostimulatory CpG motifs; modified LT and CT; MVA: modified vaccinia virus with relevant inserts; hGM-CSF; hIL-12; hIL-2; or Immudaptin: C3d tandem array (Engers et al., 2003 Vaccine volume 21: pp. 3503-3524); polyacryl starch microparticles (Wikingsson and Sjoholm, 2002 Vaccine volume 20: pp. 3355-3363)

As will be appreciated by one of skill in the art, suitable immunomodulators include but are by no means limited to: CpG oligodeoxynucleotide or CpG oligodeoxynucleotide encapsulated in liposomes (Aviva et al., 2002 Vaccine volume 20: pp. 3342-3354; Li et al., 2002 Vaccine volume 20: pp. 148-157; Mariotti et al., 2002 Vaccine volume 20: pp. 2229-2239); α2-macroglobulin (Cianciolo et al., 2002 Vaccine volume 20: pp. 554-562); various polysaccharide compounds, for example, various forms of β glucans, zwitterionic polysaccharides such as polysaccharide A from the anaerobic bacterium *Bacteroides fragilis*, mannans, hyaluronic acids (Tzianabos, 2000 Clinical Microbiology Review volume 13: pp. 523-533), and immune cell targeting strategies (Berry, J. D., Licea, A., Popkov, M., Cortez, X., Fuller, R., Elia, M., Kerwin, L., and C. F. Barbas III. (2003) Rapid monoclonal antibody generation via dendritic cell targeting in vivo. Hybridoma and Hybridomics 22 (1), 23-31).

Eleven hybridoma clones expressing high titres of rPA-specific MAbs were identified, and all were of the IgG1/k isotype. After assaying all of the clones via an initial in vitro LeTx neutralization assay, three hybridoma clones F20G75, F20G76, and F20G77, were chosen for further study. Sequencing of the expressed $V_H$ and $V_L$ region cDNAs indicates that these were distinct hybridomas formed by the immortalisation of B cells with uniquely rearranged V genes (Corbett et al., manuscript in preparation). To determine the nature of the rPA epitopes recognized by the anti-rPA MAbs, Western immunoblots were performed in duplicate; a representative immunoblot is shown in FIG. 1. All of the MAbs recognized an approximately 83 kDa protein that corresponds to mature rPA, and showed no cross-reactivity with either rLF or BSA. Binding to denatured protein suggests that these MAbs recognize a linear epitope (Cohen et al., 1986). The endpoint ELISA titre of the neutralizing MAbs specific for rPA (coated at 100 ng/well) was defined by the lowest MAb dilution resulting in a five-fold higher OD reading than the background reading obtained against BSA (Table 1). Specificity was good, with no significant reaction to rLF or BSA. Measurement of the affinity of the MAbs for rPA was performed via surface plasmon resonance analysis. As shown in Table 1, the $K_D$ for each MAb binding to rPA was in the nM range. The $k_{on}$ value for each MAb was nearly identical, however F20G77 exhibited a significantly lower $k_{off}$ rate, which greatly increased its apparent affinity for rPA.

To identify the rPA epitopes recognized by the MAbs, overlapping pin-peptides covering the entire sequence of PA were employed for epitope mapping. Each MAb reacted strongly to the same set of three overlapping 15-mers (FIG. 2), extending from S301 to S325. The core motif common to all three 15-mer peptides is $^{311}$ASFFD$^{315}$. In the crystal structure of mature PA alone (Petosa et al., 1997), and in complex with receptor CMG2 (Santelli et al., 2004), the region of the 2β2-2β3 loop extending from H304 to S319, encompassing most of the above noted epitopes of the F20G75/76/77 MAbs, remains unresolved due to its flexibility. Within the PA63 heptamer, this region undergoes structural rearrangements in the acidified endosome, leading to the production of a predicted extended β-barrel that spans the endosomal membrane (Petosa et al., 1997; Benson et al., 1998; Nassi et al., 2002; Santelli et al., 2004). Indeed, specific residues in the region extending from V303 to D315 (Qa'dan et al., 2005), including F313 and F314 (Singh et al., 1994; Benson et al., 1998) are involved in LF translocation, supporting the model that the 2β2-2β3 loop is involved in β-barrel formation. The $^{313}$FFD$^{315}$ site in PA domain 2 is sensitive to chymotrypsin cleavage (Novak et al., 1992; Singh et al., 1994), suggesting that a portion of the flexible 2β2-2β3 loop containing these residues is solvent exposed in the PA monomer (Singh et al., 1994). rPA was subjected to digestion by trypsin and chymotrypsin and MAb binding to the proteolytic fragments was assayed via Western immunoblot. Trypsin cleaves PA at the $^{164}$RKKR$^{167}$ sequence in domain 1, resulting in 63 and 20 kDa fragments (Novak et al., 1992), while chymotrypsin cleavage at the $^{313}$FFD$^{315}$ sequence in domain 2 results in 47 and 37 kDa fragments (Singh et al., 1994). As shown in FIG. 3, trypsin cleavage had no effect on MAb recognition of the 63 kDa fragment of rPA, while chymotrypsin cleavage completely abrogated MAb binding, confirming that the epitope of all three MAbs extends across the $^{313}$FFD$^{315}$ sequence in domain 2. This observation, coupled with the fact that three MAbs were developed that recognize the flexible 2β2-2β3 loop, lends support to the prediction that this region is exposed on the surface of PA.

To determine whether any particular residues in the identified PA domain 2 epitope were critical for MAb binding, a set of 15-mer pin-peptides was synthesized such that every residue extending from N306 to V320 was changed in turn to Ala (or in the case of existing Ala residues, to Gly). These peptides were assessed in the same manner as described for the epitope mapping employing overlapping peptides covering the whole PA sequence. As shown in FIG. 4, alteration of residues extending from A311 to D315 reduced MAb binding significantly, with F313A, F314A, and D315A having the most apparent effect. The presence of two bulky, hydrophobic Phe residues in the middle of this epitope likely creates a specific peptide conformation that is critical for MAb recognition (Alvord, Jr. et al., 1986; Warren et al., 1995). Interestingly, changing H310 to Ala increased apparent MAb binding efficiency by approximately two-fold. The H310 residue in the epitope may constrain folding of the peptide via interaction with F314 or F315 (Yoshida et al., 2000), and, as opposed to the case of the F314A and F315A replacements, the H310A replacement might result in an alternate structural peptide conformation that leads to more efficient MAb binding.

In vitro neutralization assays were employed to quantitatively assay the ability of the MAbs to neutralize LeTx. The neutralizing titres were determined by the lowest MAb concentration that resulted in an OD reading of at least 90-100% of that of the cell control samples (containing no toxin). Two formats of the same assay were employed. In the first, MAbs were co-incubated with rPA and rLF prior to addition of the LeTx to the cells, while in the second, rPA was allowed to bind to the J774A.1 cells prior to addition of MAbs and rLF.

Using the first assay format, the MAbs all neutralized LeTx, exhibiting neutralizing titres of 12.5 ng ml$^{-1}$ (F20G75), 11.8 ng ml$^{-1}$ (F20G76), and 16.0 ng ml$^{-1}$ (F20G77). Another MAb, raised against a non-anthrax protein antigen, served as a negative control, and exhibited no neutralization activity. Interestingly, neutralization did not appear to be dose-responsive (Laffly et al., 2005; Brossier et al., 2004). Rather, neutralization appeared to be an "all or nothing" event, with the ability of each MAb to neutralize LeTx remaining high at concentrations of 12-16 ng ml$^{-1}$, until a dramatic decrease occurred once the MAbs were diluted to a concentration approaching 5-7 ng ml$^{-1}$. This might be due to a strictly defined "threshold" concentration of MAb molecules required to bind the specific epitope in rPA and inhibit LeTx activity. Once this minimal threshold level of MAb molecules is present in the local environment where PA, LF, and the toxin receptor are present, LeTx activity is completely abrogated, and the presence of more MAbs in the environment causes no increase in neutralization. Alternatively, the high affinity of the neutralizing MAbs for PA might affect the dose responsiveness of the observed in vitro LeTx neutralization. As noted previously, an affinity enhanced PA-specific neutralizing MAb ($K_D$ for PA binding 0.33 nM) exhibited a much steeper LeTx neutralization dose response curve compared to the parental MAb ($K_D$ for PA binding 3.5-3.7 nM) from which it was derived (Mohamed et al., 2005). Similarly, a high affinity (pM range) PA-specific neutralizing MAb lacking an Fc region exhibited a steep LeTx neutralization dose response curve, although a different cell line was employed in that study (Mabry et al., 2005). Nevertheless, these reports do suggest that higher affinity anti-PA MAbs (or scAbs) can result in characteristically steep LeTx in vitro neutralization dose responsiveness. Using the second assay format, in which rPA was allowed to incubate with the J774A.1 macrophage cells prior to the addition of MAbs and rLF, some neutralization of LeTx was evident. However, MAb concentrations approaching 1-10 μg ml$^{-1}$ were required for significant levels of neutralization to occur, and in some cases the OD readings in the presence of the MAbs in this second assay format only approached, but did not exceed, a level of 90% compared to the no-toxin controls. This observation indicates that neutralization was considerably more effective when the MAbs were able to bind to rPA prior to addition of the LeTx to the cells, and suggests that these MAbs cannot efficiently bind directly to rPA on the cell surface. Thus, it is probable that the MAbs do not act by blocking LF binding to surface-bound PA. In support of this observation, the H304-S319 "insertion loop," which contains the epitope recognized by MAbs F20G75/76/77, is essentially buried between neighbouring monomers in the heptameric prepore (Lacy et al., 2004), which would likely restrict MAb access to the epitope.

Several methods of neutralization can be envisaged for MAbs F20G75, F20G76, and F20G77. In one scenario, binding of the MAbs to the predicted surface exposed epitope within the 2β2-2β3 loop of PA might result in regional conformational changes in PA that would prevent efficient receptor binding. An examination of the co-crystal structure of PA with CMG2 reveals that key interactions are made between the β3-β4 loop of domain 2 and CMG2 (Santelli et al., 2004), and since the 2β2-2β3 loop is in close proximity to the β3-β4 loop, binding of MAbs to the 2β2-2β3 loop might disrupt PA:receptor binding. Alternatively, binding of the MAbs to this region might create steric hindrance that either directly blocks access of PA to its receptor, or, more likely, prevents heptamerization after receptor binding. In this latter scenario, one can reason that MAb binding to the above noted epitope within the 2β2-2β3 loop region of PA could prevent the interaction of this domain with its nearest neighbour in the heptamer by creating a physical barrier to inter-subunit binding. Regardless of which specific mechanism results in LeTx neutralization, it is clear from the data presented herein that these MAbs most likely neutralize LeTx at a step prior to the interaction of PA with its receptor and subsequent heptamer formation on the cell surface.

The data presented here suggest that domain 2 of PA is an immunogenic target for the development of LeTx neutralizing MAbs, and that the 2β2-2β3 loop of domain 2 in rPA is solvent accessible on the surface of the PA monomer. Coincidentally, the importance of amino acid residues $^{312}$SFFD$^{315}$ within this region was recently confirmed using phage peptide display techniques (Zhang et al., 2006). The observations summarized herein will aid in the development of immunodiagnostic reagents and subunit vaccine candidates for the detection and treatment of B. anthracis infection.

While not wishing to be bound to a particular theory, it is believed that the most likely mechanism of the MAbs is to prevent heptamerization of the PA63 protein, at least in vitro in solution.

We now know definitively that passive administration of at least F20G77 protects Fisher brown rats from challenge with a lethal dose of lethal toxin.

The invention will now be explained by way of example; however, it is to be understood that the examples are for illustrative purposes and do not necessarily limit the invention.

2. Materials and Methods 2.1 Mouse immunization protocol and MAb production. For antibody production, pairs of five to six week old BALB/c mice (Charles River, Wilmington, Mass.) were inoculated (day 1) subcutaneously with 5 μg of rPA (produced as described in Miller et al., 1999) in phosphate buffered saline (PBS; pH 7.2), mixed with an equal volume of Complete Freund's Adjuvant (Difco, BD Biosciences, Oakville, ON). Subcutaneous boosters of 5 μg of rPA in PBS mixed with an equal portion of Incomplete Freund's Adjuvant (Difco) were performed on days 30, 48, and 63. The mice were given a final intraperitoneal boost of 3 μg of rPA in PBS and euthanized three days later. The rPA-specific humoral immune response was monitored via enzyme linked immunosorbent assays (ELISA) using sera collected from the mice during the inoculation protocol, as described in (Berry et al., 2004), except the 96-well ELISA plates (MaxiSorp™, Nalge-NUNC, Rochester, N.Y.) were coated with either rPA or, as a negative control, bovine serum albumin (BSA), both at 100 ng/well. Once sufficient anti-rPA titres were detected (OD$_{405}$ in ELISA at least three-fold above background), the mice were euthanized, and hybridoma production and growth proceeded as described (Berry et al., 2004). MAb harvesting, concentration, and isotyping were performed as described previously (Berry et al., 2004). Hybridoma supernatants were screened via the same ELISA to identify clones expressing high titres (OD$_{405}$ in ELISA equal to or greater than that observed in the mouse immune serum) of rPA-specific MAbs. Mouse immune and pre-immune sera (diluted 1:2000 with 0.2% BSA in PBS) served as positive and negative controls, respectively. The MAbs were purified using HiTrap™ Protein G HP columns according to the manufacturer's instructions (Amersham Biosciences, Uppsala, Sweden), the buffer was exchanged with PBS, and the MAb concentrations were determined with a Micro BCA Protein Assay Kit according to the manufacturer's instructions (Pierce, Rockford, Ill.).

For comparison purposes, murine hybridomas producing monoclonal antibodies to anthrax protective antigen were obtained from Stephen Little of the US Army Medical Research Institute of Infectious Diseases (USAMRIID). These hybridomas were grown-up and monoclonal antibodies purified from each and were tested. These were used as positive controls for the development of our own hybridomas.

2.2 In vitro LeTx neutralization assays. Lethal toxin (LeTx) neutralization was tested in vitro using the LeTx-sensitive mouse macrophage cell line J774A.1 (ATCC, Manassas, Va.), essentially as described (Laffly et al., 2005). Briefly, the mouse macrophage adherent cell line J774A.1 was seeded at $10^5$ cells ml$^{-1}$ into the wells of a 96-well culture plate (96 Well Clear Flat Bottom Polystyrene TC-Treated Microplate, Corning, N.Y.), and grown overnight in BD Cell™ MAb Medium, Quantum Yield (BD Biosciences, Bedford, Mass.) supplemented with 10% standard FBS (Hy-Clone, Logan, Utah), 1% L-glutamine, and 1× antibiotic-antimycotic solution (Wisent, St. Bruno, QC) at 37° C. in a 5% $CO_2$ atmosphere. After overnight incubation the culture supernatant was removed from each well in the 96-well culture plate. In a separate 96-well ELISA plate, 100 μl aliquots of hybridoma supernatants (undiluted) or MAbs (diluted 1:10 to 1:100,000 in PBS) were added to appropriate wells. Into each test well containing diluted MAbs, 100 μl of a mixture of 2.0 μg ml$^{-1}$ rPA and 1.0 μg ml$^{-1}$ rLF (produced as described in Kassam et al., 2005) diluted in PBS, was added. Cell control wells contained PBS only, and did not receive any toxin or MAb, and toxin control wells contained toxin but no MAbs. This ELISA plate was then incubated at 37° C. for one hour. 100 μl aliquots of each dilution of each MAb containing toxin (or appropriate toxin or cell control) was then transferred from the ELISA plate into the wells of the 96-well culture plate containing the adherent J774A.1 cells. This plate was then incubated at 37° C. for 2 hours, whereupon 100 μl of fresh growth medium and 40 μl of CellTiter 96® AQ$_{ueous}$ One Solution Cell Proliferation Assay medium (Promega, Madison, Wis.) were added. The cells were incubated for a further 2-2.5 hours at 37° C. to allow for colour development, and the plate scanned in an ELISA plate reader at 490 nm. In a second assay, appropriately diluted rPA was added to the J774A.1 cells in the absence of any MAb, and the cells were incubated for one hour at 37° C. The MAbs were separately combined with rLF and incubated at 37° C. for one hour, and then applied to the cells to which the PA was already added. All component concentrations, dilutions, incubations, and other relevant conditions in this second assay format were as outlined above. The lowest MAb dilution that resulted in an $OD_{490}$ reading equal to 90% or greater of the no-toxin control was used to determine the neutralizing titre. All neutralization assays were performed at least in triplicate.

2.3 Endpoint ELISA determinations. rPA, rLF, and BSA were diluted in PBS (pH 7.2) and each was coated at 100 ng/well in 96-well ELISA plates at 4° C. overnight. The plates were then blocked with 10% skim milk in PBS for 90 minutes at 37° C., followed by three washes with 0.9% NaCl/0.05% Tween-20. MAbs were diluted (1:10 to 1:10$^{10}$) in 2% BSA/PBS, applied to the wells, and incubated at 37° C. for 90 minutes. The wells were then washed four times, and incubated with the secondary antibody (horseradish peroxidase (HRP) conjugated goat anti-mouse IgG F(ab')$_2$, Jackson ImmunoResearch, West Grove, Pa.) diluted 1:5000 in 2% BSA/PBS, at 37° C. for 90 minutes. The wells were washed four times, and then colour development was monitored for 15 to 60 minutes after the addition of 200 μl of ABTS developing solution (Roche Diagnostics, Indianapolis, Ind.), followed by scanning at 405 nm on an ELISA plate reader. All endpoint ELISA determinations were performed at least twice.

2.4 SDS-PAGE and Western Immunoblotting. Immunoblots were performed essentially as described in (Berry et al., 2004). Briefly, 2 μg of rPA (or proteolytic digests thereof) were mixed with 10-20 μl of SDS-PAGE loading buffer (Bio-Rad, Hercules, Calif.), boiled for 5 minutes, and electrophoresed at 200V for one hour on a 4-20% Criterion Precast polyacrylamide gel (Bio-Rad) followed by electrophoretic transfer to nitrocellulose for one hour at 100 V. Equal amounts of BSA and rLF were included as negative controls. Blocking proceeded for one hour at room temperature in blocking buffer (10% skim milk in Tris-buffered saline/0.1% Tween-20 (TBST)). MAbs were diluted 1:5000 in blocking buffer, and applied to the blots overnight at 4° C. The blots were washed with TBST as described in (Berry et al., 2004), incubated at room temperature for one hour with a HRP conjugated goat anti-mouse IgG F(ab')$_2$ (Jackson ImmunoResearch, West Grove, Pa.) diluted 1:5000 with blocking buffer, and finally washed as described (Berry et al., 2004). Development was performed using either 4-chloro-1-napthol substrate (Sigma) directly, or ECL Plus™ chemiluminescent detection reagent followed by exposure to Hyperfilm™ ECL™ (Amersham Biosciences, Piscataway, N.J.), according to the manufacturers' instructions. Blots probed with rabbit serum were treated as described above, except they were incubated with a 1:5000 dilution of immune serum from rabbits inoculated with rPA, and the secondary antibody used for detection was HRP conjugated goat anti-rabbit IgG (Jackson ImmunoResearch). All immunoblots were performed in duplicate.

2.5 Pin-peptide epitope mapping. Peptides covering the entire length of PA were synthesized as 15-mers, overlapping by ten residues, coupled to nylon support pins in a 96-well format (Pepscan Systems, Lelystad, the Netherlands). All manipulations of the pin-peptide assemblies were performed by placing the tips of the pins in the wells of ELISA plates (MaxiSorp™, Nalge-NUNC, Rochester, N.Y.), ensuring they were fully submerged in the liquid samples. The pins were blocked with 200 μl of 4% BSA/PBS for 2 hours at room temperature, followed by three washes with 0.9% NaCl/0.05% Tween 20 buffer. The pins were incubated with the MAbs (diluted to 1:500 or 1:1000 in 2% BSA/PBS) overnight at 4° C., and washed as described above. Incubation with 100 μl of HRP conjugated goat anti-mouse IgG F(ab')$_2$ (Jackson ImmunoResearch) diluted 1:5000 in 2% BSA/PBS proceeded at room temperature for 4 hours, followed by washing as described above. Colour development and scanning was performed as described for the endpoint ELISAs above. The epitope mapping experiments were performed at least twice for each MAb. The cut off value for positive binding was set at three times the average background $OD_{405}$ value.

2.6 Proteolytic digestion of PA. Trypsin (TPCK treated, from Bovine pancreas, Sigma) was dissolved in 1 mM HCl, and α-Chymotrypsin (Type VII, TLCK treated, Sigma) was dissolved in 1 mM HCl/10 mM $CaCl_2$ to make working stocks of 5 mg ml$^{-1}$. Trypsin digests were performed in a total volume of 20 μl containing 2 μg of rPA mixed with 40 ng of trypsin. The digestion buffer was 100 mM Tris-HCl (pH 8). Chymotrypsin digests were performed identically, except the digestion buffer was 100 mM Tris-HCl (pH 8)/10 mM $CaCl_2$. In both cases, the reactions were incubated on ice for 10 minutes, whereupon 2 μl of a 1 mg ml$^{-1}$ solution of trypsin-chymotrypsin inhibitor (from soybean, Sigma) was added to stop the reactions. All proteolysis experiments were performed in duplicate.

2.7 MAb affinity analysis via surface plasmon resonance. The measurement of the MAbs' affinity for rPA was performed essentially as described (Karlsson et al., 1991; Mabry et al., 2005) using a Biacore 2000 instrument (Biacore, Uppsala, Sweden). All solutions were purchased from Biacore. Briefly, a single flow cell on a CM5 sensor chip was activated by the addition of 20 µl of a 1:1 mixture of 1-ethyl-3(3-dimethylaminopropyl)-carbodiimide hydrochloride:N-hydroxysuccinimide (EDC:NHS). 10 µl of a 2.7 mg ml$^{-1}$ solution of rPA was diluted in sodium-acetate (pH 4), and 20 µl of this solution was coated on the activated chip. The chip was then blocked by the addition of 35 µl of ethanolamine-HCl, followed by a wash with 35 µl of 10 mM glycine-HCl (pH 1.5). The anti-PA MAbs were diluted in HBS-P buffer to final concentrations ranging from 889 to 2200 nM, and 40 µl of each dilution (five dilutions in total for each MAb) were applied in turn to the rPA-coated flow cell. The flow cell surface was regenerated in between additions of antibody dilutions via a wash with 35 µl of 10 mM glycine-HCl (pH 1.5). BIAevaluation 3.2 software was used to measure and plot the $k_{on}$ and $k_{off}$ values directly, which were then used to calculate the affinity ($K_D$).

Synthetic peptides that represent portions of the anthrax protective antigen were synthesized and obtained from United Biochemicals Research Ltd. (Seattle, Wash., USA). They were conjugated to BSA or KLH {Keyhole Limpet Hemocyanin} using methods and reagents in the Imject Maleimide Activated Immunogen Conjugation kit (Pierce Biotechnology, Inc., Rockford, Ill., USA) for use as antigen in standard indirect ELISA or as immunogen for immunization of animals respectively.

Immunization of animals with synthetic peptides conjugated to KLH will be done according to standard in-house laboratory animal procedures using Institute Animal Care Committee approved protocol.

While the preferred embodiments of the invention have been described above, it will be recognized and understood that various modifications may be made therein, and the appended claims are intended to cover all such modifications which may fall within the spirit and scope of the invention.

References

Abrami L, Liu S, Cosson P, Leppla S H & van der Goot F G (2003) Anthrax toxin triggers endocytosis of its receptor via a lipid raft-mediated clathrin-dependent process. *J. Cell Biol.* 160: 321-328.

Abrami L, Reig N, & van der Goot F G (2005) Anthrax toxin: the long and winding road that leads to the kill. *Trends Microbiol.* 13: 72-78.

Adams T, Osborn S, & Rijpkema S (2005) An immunodiffusion assay to assess the protective antigen content of anthrax vaccine. *Vaccine* 23: 4517-4520.

Alvord E C Jr., Hruby S, Martenson R E, Deibler G E, & Law M J (1986) Evidence for specific polypeptide chain folding in myelin basic protein from reactions between fragments of the protein and monoclonal antibodies. *J. Neurochem.* 47: 764-771.

Baillie L, Townend T, Walker N, Eriksson U, & Williamson D (2004) Characterization of the human immune response to the UK anthrax vaccine. *FEMS Immunol. Med. Microbiol.* 42: 267-270.

Benson E L, Huynh P D, Finkelstein A, & Collier R J (1998) Identification of residues lining the anthrax protective antigen channel. *Biochemistry* 37: 3941-3948.

Berry J D, Jones S, Drebot M A, et al. (2004) Development and characterisation of neutralising monoclonal antibody to the SARS-coronavirus. *J. Virol. Methods* 120: 87-96.

Bradley K A, Mogridge J, Mourez M, Collier R J, & Young J A (2001) Identification of the cellular receptor for anthrax toxin. *Nature* 414: 225-229.

Brossier F, Levy M, Landier A, Lafaye P, & Mock M (2004) Functional analysis of *Bacillus anthracis* protective antigen by using neutralizing monoclonal antibodies. *Infect. Immun.* 72: 6313-6317.

Chauhan V & Bhatnagar R (2002) Identification of amino acid residues of anthrax protective antigen involved in binding with lethal factor. *Infect. Immun.* 70: 4477-4484.

Cohen G H, Isola V J, Kuhns J, Berman P W, & Eisenberg R J (1986) Localization of discontinuous epitopes of herpes simplex virus glycoprotein D: use of a nondenaturing ("native" gel) system of polyacrylamide gel electrophoresis coupled with western blotting. *J. Virol.* 60: 157-166.

Cunningham K, Lacy D B, Mogridge J, & Collier R J (2002) Mapping the lethal factor and edema factor binding sites on oligomeric anthrax protective antigen. *Proc. Natl. Acad. Sci. USA* 99: 7049-7053.

Karlsson R, Michaelsson A, & Mattsson L (1991) Kinetic analysis of monoclonal antibody-antigen interactions with a new biosensor based analytical system *J. Immunol. Methods* 145: 229-240.

Kassam A, Der S D, & Mogridge J (2005) Differentiation of human monocytic cell lines confers susceptibility to *Bacillus anthracis* lethal toxin. *Cell Microbiol.* 7: 281-292.

Lacy D B, Wigelsworth D J, Melnyk R A, Harrison S C, & Collier R J (2004) Structure of heptameric protective antigen bound to an anthrax toxin receptor: a role for receptor in pH-dependent pore formation. *Proc. Natl. Acad. Sci. USA* 101: 13147-13151.

Laffly E, Danjou L, Condemine F, Vidal D, Drouet E, Lefranc M P, Bottex C, & Thullier P (2005) Selection of a macaque Fab with framework regions like those in humans, high affinity, and ability to neutralize the protective antigen (PA) of *Bacillus anthracis* by binding to the segment of PA between residues 686 and 694. *Antimicrob. Agents Chemother.* 49: 3414-3420.

Leppla S H, Robbins J B, Schneerson R, & Shiloach J (2002) Development of an improved vaccine for anthrax. *J. Clin. Invest* 110: 141-144.

Little S F, Leppla S H, & Cora E (1988) Production and characterization of monoclonal antibodies to the protective antigen component of *Bacillus anthracis* toxin. *Infect. Immun.* 56: 1807-1813.

Little S F, Ivins B E, Fellows P F, Pitt M L, Norris S L, & Andrews G P (2004) Defining a serological correlate of protection in rabbits for a recombinant anthrax vaccine. *Vaccine* 22: 422-430.

Little S F, Novak J M, Lowe J R, Leppla S H, Singh Y, Klimpel K R, Lidgerding B C, & Friedlander A M (1996) Characterization of lethal factor binding and cell receptor binding domains of protective antigen of *Bacillus anthracis* using monoclonal antibodies. *Microbiology* 142: 707-715.

Liu S & Leppla S H (2003) Cell surface tumor endothelium marker 8 cytoplasmic tail-independent anthrax toxin binding, proteolytic processing, oligomer formation, and internalization. *J. Biol. Chem.* 278: 5227-5234.

Mabry R, Rani M, Geiger R, Hubbard G B, Carrion R, Jr., Brasky K, Patterson J L, Georgiou G, & Iverson B L (2005) passive protection against anthrax by using a high-affinity antitoxin antibody fragment lacking an Fc region. *Infect. Immun.* 73: 8362-8368.

Miller C J, Elliott J L, & Collier R J (1999) Anthrax protective antigen: prepore-to-pore conversion. *Biochemistry* 38: 10432-10441.

Miller J, McBride B W, Manchee R J, Moore P, & Baillie L W (1998) Production and purification of recombinant protective antigen and protective efficacy against *Bacillus anthracis*. *Lett. Appl. Microbiol.* 26: 56-60.

Milne J C, Furlong D, Hanna P C, Wall J S, & Collier R J (1994) Anthrax protective antigen forms oligomers during intoxication of mammalian cells. *J. Biol. Chem.* 269: 20607-20612.

Mogridge J, Mourez M, & Collier R J (2001) Involvement of domain 3 in oligomerization by the protective antigen moiety of anthrax toxin. *J. Bacteriol.* 183: 2111-2116.

Mogridge J, Cunningham K, Lacy D B, Mourez M, & Collier R J (2002) The lethal and edema factors of anthrax toxin bind only to oligomeric forms of the protective antigen. *Proc. Natl. Acad. Sci. USA* 99: 7045-7048.

Mohamed N, Clagett M, Li J, Jones S, Pincus S, D'Alia G, Nardone L, Babin M, Spitalny G, & Casey L (2005) A high-affinity monoclonal antibody to anthrax protective antigen passively protects rabbits before and after aerosolized *Bacillus anthracis* spore challenge. *Infect. Immun.* 73: 795-802.

Molloy S S, Bresnahan P A, Leppla S H, Klimpel K R, & Thomas G (1992) Human furin is a calcium-dependent serine endoprotease that recognizes the sequence Arg-X-X-Arg and efficiently cleaves anthrax toxin protective antigen. *J. Biol. Chem.* 267: 16396-16402.

Nassi S, Collier R J, & Finkelstein A (2002) PA63 channel of anthrax toxin: an extended beta-barrel *Biochemistry* 41: 1445-1450.

Novak J M, Stein M P, Little S F, Leppla S H, & Friedlander A M (1992) Functional characterization of protease-treated *Bacillus anthracis* protective antigen. *J. Biol. Chem.* 267: 17186-17193.

Okinaka R T, Cloud K, Hampton O, et al. (1999) Sequence and organization of pXO1, the large *Bacillus anthracis* plasmid harboring the anthrax toxin genes. *J. Bacteriol.* 181: 6509-6515.

Petosa C, Collier R J, Klimpel K R, Leppla S H, & Liddington R C (1997) Crystal structure of the anthrax toxin protective antigen. *Nature* 385: 833-838.

Pitt M L, Little S F, Ivins B E, Fellows P, Barth J, Hewetson J, Gibbs P, Dertzbaugh M, & Friedlander A M (2001) In vitro correlate of immunity in a rabbit model of inhalational anthrax. *Vaccine* 19: 4768-4773.

Qa'dan M, Christensen K A, Zhang L, Roberts T M, & Collier R J (2005) Membrane insertion by anthrax protective antigen in cultured cells *Mol. Cell. Biol.* 25: 5492-5498.

Reuveny S, White M D, Adar Y Y, Kafri Y, Altboum Z, Gozes Y, Kobiler D, Shafferman A, & Velan B (2001) Search for correlates of protective immunity conferred by anthrax vaccine *Infect Immun.* 69: 2888-2893.

Santelli E, Bankston L A, Leppla S H, & Liddington R C (2004) Crystal structure of a complex between anthrax toxin and its host cell receptor. *Nature* 430: 905-908.

Scobie H M, Rainey G J, Bradley K A, & Young J A (2003) Human capillary morphogenesis protein 2 functions as an anthrax toxin receptor. *Proc. Natl. Acad. Sci. USA* 100: 5170-5174.

Singh Y, Chaudhary V K, & Leppla S H (1989) A deleted variant of *Bacillus anthracis* protective antigen is nontoxic and blocks anthrax toxin action in vivo. *J. Biol. Chem.* 264:19103-19107.

Singh Y, Klimpel K R, Quinn C P, Chaudhary V K, & Leppla S H (1991) The carboxyl-terminal end of protective antigen is required for receptor binding and anthrax toxin activity. *J. Biol. Chem.* 266: 15493-15497.

Singh Y, Klimpel K R, Arora N, Sharma M, & Leppla S H (1994) The chymotrypsin-sensitive site, FFD315, in anthrax toxin protective antigen is required for translocation of lethal factor. *J. Biol. Chem.* 269: 29039-29046.

Turnbull P C, Broster M G, Carman J A, Manchee R J, & Melling J (1986) Development of antibodies to protective antigen and lethal factor components of anthrax toxin in humans and guinea pigs and their relevance to protective immunity. *Infect Immun.* 52: 356-363.

Varughese M, Teixeira A V, Liu S, & Leppla S H (1999) Identification of a receptor-binding region within domain 4 of the protective antigen component of anthrax toxin. *Infect Immun.* 67: 1860-1865.

Warren K G, Catz I, & Steinman L (1995) Fine specificity of the antibody response to myelin basic protein in the central nervous system in multiple sclerosis: the minimal B-cell epitope and a model of its features. *Proc. Natl. Acad. Sci. USA* 92: 11061-11065.

Yoshida H, Matsushima N, Kumaki Y, Nakata M, & Hikichi K (2000) NMR studies of model peptides of PHGGGWGQ repeats within the N-terminus of prion proteins: a loop conformation with histidine and tryptophan in close proximity. *J. Biochem. (Tokyo)* 128: 271-281.

Zhang J, Xu J, Li G, Dong D, Song X, Guo Q, Zhao J, Fu L, & Chen W (2006) The 2β2-2β3 loop of anthrax protective antigen contains a dominant neutralizing epitope. *Biochem Biophys Res Commun.* 341:1164-71

TABLE 1

Endpoint ELISA titres and affinity of the rPA-specific MAbs.

| MAb | Relevant properties | | | |
| --- | --- | --- | --- | --- |
| | Endpoint ELISA titre (ng ml$^{-1}$)$^a$ | $k_{on}$ for rPA binding ($10^3$ M$^{-1}$ s$^{-1}$)$^b$ | $k_{off}$ for rPA binding ($10^{-5}$ s$^{-1}$)$^b$ | Affinity ($K_D$) for rPA binding (nM)$^b$ |
| F20G75 | 20 | 3.4 ± 0.76 | 6.9 ± 0.40 | 20.8 ± 4.6 |
| F20G76 | 20 | 4.0 ± 1.2 | 6.8 ± 0.25 | 18.5 ± 5.9 |
| F20G77 | 20 | 3.1 ± 0.72 | 0.14 ± 0.013 | 0.46 ± 0.14 |

$^a$Average of three replicates.
$^b$Average of at least three replicates, ± standard deviation.

The invention claimed is:

1. A method of neutralizing *Bacillus anthracis* protective antigen (PA) in an individual comprising administering to said individual an effective amount of a pharmaceutical composition comprising a *Bacillus anthracis* neutralizing monoclonal antibody that binds *Bacillus anthracis* PA, said antibody selected from the group consisting of: F20G75, comprising a light chain variable region consisting of the amino acid sequence as set forth in SEQ ID NO: 10 and a heavy chain variable region consisting of the amino acid sequence set forth in SEQ ID NO: 16; F20G76, comprising a light chain variable region consisting of the amino acid sequence as set forth in SEQ ID NO: 12 and a heavy chain variable region consisting of the amino acid sequence as set forth in SEQ ID NO: 18; and F20G77, comprising a light chain variable region consisting of the amino acid sequence as set forth in SEQ ID NO: 14 and a heavy chain variable region consisting of the amino acid sequence as set forth in SEQ ID NO: 20; and wherein the pharmaceutical composition comprises a suitable excipient.

2. The method according to claim 1 wherein the monoclonal antibody is F20G75.

3. The method according to claim 1 wherein said monoclonal antibody binds PA at an epitope comprising the amino acid sequence ASFFDI (SEQ ID NO:2).

* * * * *